US012612467B2

(12) United States Patent
Simon

(10) Patent No.: US 12,612,467 B2
(45) Date of Patent: Apr. 28, 2026

(54) TREATMENT OF NECROTIZING ENTEROCOLITIS WITH SEMISYNTHETIC POLYCLONAL HUMAN SECRETORY IMMUNOGLOBIN A

(71) Applicant: Michael R. Simon, Ann Arbor, MI (US)

(72) Inventor: Michael R. Simon, Ann Arbor, MI (US)

( * ) Notice: Subject to any disclaimer, the term of this patent is extended or adjusted under 35 U.S.C. 154(b) by 370 days.

(21) Appl. No.: 17/949,398

(22) Filed: Sep. 21, 2022

(65) Prior Publication Data

US 2024/0092940 A1 Mar. 21, 2024

(51) Int. Cl.
| | |
|---|---|
| *A61P 37/06* | (2006.01) |
| *A61K 47/42* | (2017.01) |
| *A61P 1/00* | (2006.01) |
| *C07K 16/42* | (2006.01) |
| *A61K 39/00* | (2006.01) |

(52) U.S. Cl.
CPC .......... *C07K 16/4258* (2013.01); *A61K 47/42* (2013.01); *A61P 1/00* (2018.01); *A61P 37/06* (2018.01); *A61K 2039/545* (2013.01); *A61K 2039/55* (2013.01)

(58) Field of Classification Search
None
See application file for complete search history.

(56) References Cited

U.S. PATENT DOCUMENTS

| | | | | |
|---|---|---|---|---|
| 10,221,233 | B2 * | 3/2019 | Corthésy | ................. A61P 31/04 |
| 2011/0305753 | A1 * | 12/2011 | Simon | .................... A61K 39/40 |
| | | | | 424/178.1 |

OTHER PUBLICATIONS

N Engl J Med 1988;319:1-7 (Year: 1988).*
Clinics vol. 61, Issue 2, Apr. 2006, pp. 153-160 (Year: 2006).*
J. Agric. Food Chem. 2007,55, 2911-2917 (Year: 2007).*
Autoimmunity: From Bench to Bedside. Anaya JM, Shoenfeld Y, Rojas-Villarraga A, et al., editors. Bogota (Colombia): El Rosario University Press; Jul. 18, 2013. (Year: 2013).*
Biochimie 2020 vol. 177, pp. 213-225 (Year: 2020).*
Adjuvants are defined as a substance that enhances the body's immune response to an antigen (Cambridge Dictionary downloaded on Feb. 4, 2025). (Year: 2025).*
Acta Paediatr Suppl 396: 37-40. 1994 (Year: 1994).*
Journal of Allergy and Clinical Immunology, vol. 143, Issue 2, AB233, (Year: 2019).*
The Lactiga Platform. Transforming Treatment Across Disease States. 3 pp., dated Jul. 29, 2021.
Latiga. Mucosal IGA is the Next Frontier of Immunity. 8 pp., dated Jul. 29, 2021.

* cited by examiner

Primary Examiner — Rachel B Gill
Assistant Examiner — Imma Barrera
(74) Attorney, Agent, or Firm — MaxGoLaw PLLC

(57) ABSTRACT

A process is provided for inhibiting or preventing symptoms of necrotizing enterocolitis in a subject that includes the oral administration to the subject of a human polyclonal secretory IgA formed by the conjugation of human recombinant secretory component and pooled human plasma derived dimeric and polymeric. When administered in a therapeutic quantity, symptoms of necrotizing enterocolitis in the subject are inhibited or precluded.

5 Claims, No Drawings

TREATMENT OF NECROTIZING ENTEROCOLITIS WITH SEMISYNTHETIC POLYCLONAL HUMAN SECRETORY IMMUNOGLOBIN A

GOVERNMENT SUPPORT

This invention was made with government support under DK130749 awarded by the National Institutes of Health. The government has certain rights in the invention.

FIELD OF THE INVENTION

This invention relates to a process for the treatment necrotizing enterocolitis with orally administered human secretory IgA in a subject suffering therefrom, the composition administered in the form of pharmaceutical compositions.

BACKGROUND OF THE INVENTION

Necrotizing enterocolitis is caused by inflammation of the intestines in premature infants. Necrotizing enterocolitis may be superficial effecting only the mucosal lining of the gut or may be so severe that the entire thickness of the intestinal wall is involved and there is perforation caused by the inflammation (Zani and Pierro, 2019).

The incidence of necrotizing enterocolitis is about 5% to 7% of premature infants born after fewer than 33 weeks gestation (Zani and Pierro, 2019) or weighing less than 1500 grams (Hackam and Caplan, 2018). Symptoms range from bradycardia to shock (Zani and Pierro 2019). Maternal IgA in breast milk has been found to protect premature infants from necrotizing enterocolitis (Gopalakrishna 2019; Hand, NIH published report NIH/R01-DK120697-01A1, 2020).

Probiotics have been found to contribute to prevention of this syndrome (Zani and Pierro, 2019). Medical management includes bowel rest by withholding feedings for bowel rest, and general support such as maintaining adequate ventilation and blood tissue perfusion and blood pressure, and coagulopathy, thrombocytopenia and antibiotics. (Zani and Pierro, 2019). In addition, maternal breast milk which contains secretory IgA has been found to be effective in prevention of necrotizing enterocolitis (Gopalakrishna et al., 2019). Breast milk contains secretory IgA which regulates the intestinal microbiome and facilitates intestinal homeostasis (Rogier, et al. 2014). Prospects for new treatments include hypothermia and stem cell therapy (Zani and Pierro, 2019).

The prior art has failed to explore orally administered human polyclonal secretory IgAs as a potential medicament for the treatment of necrotizing enterocolitis.

Thus, there exists a need for a human polyclonal secretory IgA therapeutic for the treatment of necrotizing enterocolitis. There also exists a need to provide such a therapeutic in a dosing form well suited for treating an affected infant.

SUMMARY OF THE INVENTION

A process is provided for inhibiting symptoms of necrotizing enterocolitis in a subject suffering therefrom that includes the oral administration of polyclonal human secretory IgA to the subject with necrotizing enterocolitis or at increased risk of necrotizing enterocolitis. When administered in a therapeutic quantity based on the subject characteristics and the type of IgA, symptoms of necrotizing enterocolitis in that subject are inhibited. The administered immunoglobulin is readily formed from polyclonal sources. This invention specifies an industrial method for the manufacture of polyclonal human secretory IgA which is not otherwise obtainable in amounts suitable for medicinal use. The IgA is readily administered in a dimeric, or polymeric form that includes recombinant human secretory component.

DETAILED DESCRIPTION OF THE PREFERRED EMBODIMENTS

The present invention has utility as a treatment or prevention of necrotizing enterocolitis. The process of treatment or prevention includes treatment with polyclonal-secretory IgA that is, dimeric or polymeric and polyclonal. Polyclonal dimeric or polymeric IgA is recoverable from the plasma fractionation waste product Cohn fraction III precipitate or equivalent (Simon, 2014). It is also recoverable from the ion exchange plasma fractionation process used to recover other plasma proteins (U.S. Pat. Nos. 9,828,418B2, 10,385,117B2, 9,828,418B2).

Because of its resistance to degradation in the gastrointestinal tract, secretory IgA (U.S. Pat. No. 9,932,392B2) can be administered by mouth. Allogeneic immunoglobulins administered directly to the gastrointestinal tract have minimal side effects because they are naturally present in the gastrointestinal tract. Dimeric and polymeric IgA according to the present invention is bound to recombinant human secretory component in order to mimic naturally secreted intestinal secretory IgA which is endogenous to the subject. The administration of the semisynthetic secretory IgA compensates for the absence of naturally secreted secretory IgA in breast milk which normally provides the secretory IgA.

As used herein, a "subject" is defined as a human.

As used herein, "dimeric and polymeric IgA" is defined as a construct that contains two or more IgA monomers plus J chain.

As the present invention uses an immunoglobulin rather than a metabolic or immunological inhibitor, an effective treatment or preventative is provided which does not disturb the body's metabolism.

The following description of the preferred embodiment(s) is merely exemplary in nature and is in no way intended to limit the invention, its application, or uses.

Secretory IgA molecules are polyclonal and dimeric or polymeric; and are all known to the art, as evidenced for example, by the references incorporated herein.

In one embodiment, the invention provides a process for medical treatment of humans involving the oral administration of secretory IgA which can be derived from a number of sources. One such source for the IgA is pooled human plasma following Cohn cold ethanol fractionation to produce fraction III precipitate as performed by those of skill in the art of protein separation. The IgA byproduct is further purified by adsorption onto jackbean lectin (jacalin) or onto an ion exchange medium in neutral or slightly acidic conditions as performed by those of skill in the art of protein purification (Kabir S, 1998; and U.S. Pat. No. 9,828,418 B2).

A more detailed description of isolation of an IgA component as a byproduct from pooled human plasma or hyperimmune pooled human plasma is as follows. Ethanol fractionation of pooled human plasma is a well-known process to prepare immunoglobulin G. Pooled human plasma is first obtained from licensed plasmapheresis centers in the United States and tested for various pathogens including the HIV virus. The first manufacturing step of most commercial immunoglobulin G preparations involves a modified cold ethanol fractionation according to Cohn to produce Cohn fraction II. In the fractionation process, many infectious viruses are eliminated from the pooled human plasma. Following fractionation, the Cohn fraction II is subjected to adsorption onto an ion exchange medium. This step may selectively reduce the IgA concentration to less than 0.1%. Such a step is important for producing immunoglobulin G for intravenous infusion into humans. The modified cold ethanol fractionation process according to Cohn is a series of fractionations using various levels of ethanol, pH, and temperature to produce a fraction II which is further treated to produce immunoglobulins as described above. In the fractionation method, pooled human plasma is first treated to produce a cryoprecipitate and cryo-supernatant. The cryo-supernatant is subjected to a first ethanol fractionation to yield a supernatant I. Supernatant I is subjected to a second ethanol fractionation to yield fraction II+III. Fraction II+III is subjected to a third ethanol fractionation procedure to yield a supernatant III and Fraction III precipitate.

The fraction III precipitate enriched in IgA is generally discarded as an unwanted byproduct. According to the invention, this unwanted IgA following affinity chromatographic purification is further treated by incubation with immobilized hydrolases to inactivate viruses and vasoactive substances. Such treatment has been proven to eliminate many viruses tested including HIV, Sindbis, and vaccinia. Other antiviral treatments, as known to those skilled in the art, are used in combination and consist of solvent detergent processes, nanofiltration and/or heat inactivation. Usually, three antiviral steps are implemented. Following incubation to remove viruses, the concentration of the active material is adjusted with sterile saline or buffered solutions to ensure a constant amount of active material per milliliter of reconstituted product. Finally, the solution with a constant amount of reconstituted product is sterilized by filtration before use.

The ethanol fractionation process according to Cohn is well known in the art and is described in Cohn et al., 1946 and in more detail in pages 576-602, Kirk-Othmer Encyclopedia of Chemical Technology, Vol. 3, second edition (1963). Alternatively, ion exchange chromatography may be used to obtain the dimeric and polymeric IgA byproduct during the manufacture of intravenous immunoglobulin. From 4% to 22% of plasma IgA is dimeric and polymeric IgA (Delacroix et al., 1981; Delacroix et al., 1983). The resulting dimeric and polymeric IgA is purified. The compositions of the invention contain, in addition to the IgA component, recombinant human secretory component. Human secretory component can be produced by recombinant techniques as described in Crottet et al., 1999. The resulting dimeric IgA is further coupled to recombinant human secretory component. In a preferred embodiment, the coupling is accomplished by forming disulfide bonds under mildly oxidizing conditions (Jones, 1998). Dimeric secretory IgA containing both J chain and secretory component is again purified by ion-exchange and size exclusion chromatography and/or ultrafiltration as described in Lullau et al., 1996; Corthesy, 1997; and Crottet et al., 1999; as performed by those of skill in the art of protein purification. Purified dimeric and polymeric secretory IgA containing recombinant human secretory component is optionally stabilized for example by the addition of human serum albumin to a final concentration of 5%. The presence of the human secretory component in the compositions of the invention leads to doses of immunoglobulin A which are physiologically effective whereas compositions without secretory component is not. Additionally, this invention specifies an industrial method for the manufacture of polyclonal human secretory IgA comprised of recombinant human secretory component plus natural human plasma-derived IgA dimers and higher polymers which would not otherwise be obtainable in quantities sufficient for commercial medicinal use.

In still other embodiments, an IgA is combined with pasteurized human milk or with human milk prepared in a bioreactor (Deng M, 2022).

The secretory IgA antibodies may be administered alone, or with various pharmaceutical adjuvants.

These compositions optionally contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and the like. Prolonged residence in the intestinal lumen of the IgA can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethylene glycols, and the like.

Solid dosage forms such as tablets, dragees, capsules, pills, and granules can be prepared with coatings and shells, such as enteric coatings and others well known in the art; as detailed, for example in U.S. Pat. Nos. 4,017,647; 4,385, 078; 4,518,433; and 4,556,552.

Such solid dosages may contain opacifying agents and can also be of such composition that they release the active compound or compounds in a certain part of the intestinal tract in a delayed manner. Examples of embedding compositions which can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl alcohol, benzyl benzoate, propylene glycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethylene glycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum or other metal hydroxides, bentonite, agar-agar and tragacanth, or mixtures of these substances, and the like.

Since the effect of the IgA antibodies is dependent on their reaching the small intestine, preferred tablets or capsules are enteric coated. Alternatively, the active IgA antibodies can themselves be microencapsulated prior to formulation. Preparation of microcapsules of IgA antibody as well as preparation of enteric coated tablets or capsules can be achieved by conventional methods as detailed above.

It is appreciated that the therapeutic amount of IgA depends on the form thereof, with forms subject to gastrointestinal degradation requiring larger doses. Typically amounts of IgA from about 0.005 mg to 50 grams per day are used and preferably, 1 mg to 40 grams per day. Generally, secretory IgA are each independently effective as a treatment when provided to the patient at about 10 grams per day. Forms of IgA that are prone to gastrointestinal degradation are typically effective in doses increased by at least 80% relative to secretory forms. For example, about 5 grams of secretory IgA could be given to a subject per day in a single dose or in divided doses 3 to 4 times per day. Preferably, multiple doses are administered with meals likely containing food allergens. It is appreciated that a physician can readily adjust the doses of the IgA to be administered based on the subject response to treatment. Many factors are considered in dose adjustments. Dosages of secretory IgA envisioned by the present invention and considered to be therapeutically effective will range from between about 5 mg to 5 g. However, it is to be understood that doses can readily be adjusted to provide appropriate amounts of the IgA antibody.

The invention is further described by reference to the following detailed examples, with exemplary process methodologies described below. These examples are not meant to limit the scope of the invention that has been set forth in the foregoing description. Variations within the concepts of the invention are apparent to those skilled in the art.

The invention is distinguished from the prior art by the derivation of its dimeric and polymeric IgA component from pooled healthy human plasma. It is further distinguished by the conjugation of the dimeric and polymeric IgA components with recombinant human secretory component which is required for its normal activity in the intestines. Importantly, this invention specifies an industrial method for the manufacture of polyclonal semisynthetic human secretory IgA which is not otherwise obtainable in amounts suitable for widespread medicinal use.

Example 1

Dimeric IgA is obtained by affinity purification from pooled healthy human plasma and conjugated with recombinant human secretory component forming secretory IgA. The secretory IgA is stabilized by the addition of human serum albumin to a final concentration of 5%. The final solution is adjusted to a therapeutic dose of 1 mg secretory IgA daily. The secretory IgA is administered daily to an infant suffering with necrotizing enterocolitis. One week after initiation of treatment, the necrotizing enterocolitis sufferer experiences diminution of his/her physiological abnormalities.

Example 2

The process of Example 1 is repeated with the secretory IgA administered enterically, at a higher daily dose of 2 mg to achieve a similar result.

REFERENCES

Berzofsky J A, Berkower I J., Epstein S L, Monoclonal Antibodies in Chapter 12, Antigen-Antibody Interactions and Monoclonal Antibodies, pp. 455-465 in Fundamental Immunology, Third Edition, W. E. Paul (ed), Raven Press, NY 1993. Berzofsky et al., Fundamental Immunology, Third Edition, 1993, pp 455-462.

Cicalese L, Duerr R H, Nalesnik M A, Heeckt P F, Lee K K, Schraut W H. Decreased mucosal IgA levels in ileum of patients with chronic ulcerative colitis. Dig Dis Sci. 1995 April; 40(4): 805-11.

Cohn E J, Strong L E, Hughes W L, Jr., Mulford D J, Ashworth J N, Melin M, Taylor H L, Preparation and Properties of Serum and Plasma Proteins IV. A System for the Separation into Fractions of the Protein and Lipoprotein Components of Biological Tissues and Fluids, J. Am. Chem. Soc. 1946; 68; 459-475.

Collins S M, Denou E, Verdu E F, Bercik P. The putative role of the intestinal microbiota in the irritable bowel syndrome. Digestive and Liver Disease 41 (2009) 850-853

Corthesy B., Recombinant Secretory IgA for Immune Intervention Against Mucosal Pathogens, Biochem. Soc. Trans. 1997, 25; 471-475.

Crottet P, Cottet S, Corthesy B. Expression, Purification and Biochemical Characterization of Recombinant Murine Secretory Component, A Novel Tool in Mucosal Immunology, Biochem. J. 1999, 341; 299-306.

Caubet J C, Nowak-Węgrzyn A. Current understanding of the immune mechanisms of food protein-induced enterocolitis syndrome. Expert Rev Clin Immunol. 2011 May; 7(3):317-27.

Delacroix D L, Hodgson H J, McPherson A, Dive C, Vaerman J P. Selective transport of polymeric immunoglobulin A in bile. Quantitative relationships of monomeric and polymeric immunoglobulin A, immunoglobulin M, and other proteins in serum, bile, and saliva. J. Clin. Invest. 1982 August; 70(2):230-41.

Delacroix D L, Elkom K B, Geubel A P, Hodgson H F, Dive C, Vaerman J P. Changes in size, subclass, and metabolic properties of serum immunoglobulin A in liver diseases and in other diseases with high serum immunoglobulin A. J. Clin. Invest. 1983 February; 71(2):358-67.

Deng M, Lv X, Liu L, Li J, Du G, Chen J, and Liu Y. Efficient Bioproduction of Human Milk Alpha-Lactalbumin in Komagataella phaffii J. Agric. Food Chem. 2022, 70, 8, 2664-2672.

Donaldson G P, Ladinsky M S, Yu K B, Sanders J G, Yoo B B, Chou W C, Conner M E, Earl A M, Knight R, Bjorkman P J, Mazmanian S K Gut microbiota utilize immunoglobulin A for mucosal colonization. Science. 2018 May 18; 360(6390):795-800.

Fadlallah J, El Kafsi H, Sterlin D, Juste C, Parizot C, Dorgham K, Autaa G, Gouas D, Almeida M, Lepage P, Pons N, Le Chatelier E, Levenez F, Kennedy S, Galleron N, de Barros J P, Malphettes M, Galicier L, Boutboul D, Mathian A, Miyara M, Oksenhendler E, Amoura Z, Doré J, Fieschi C, Ehrlich S D, Larsen M, Gorochov G. Microbial ecology perturbation in human IgA deficiency. Sci Transl Med. 2018 May 2; 10(439).

Frossard C P, Hauser C, Eigenmann P A. Antigen-specific secretory IgA antibodies in the gut are decreased in a mouse model of food allergy. J Allergy Clin Immunol. 2004 August; 114(2):377-82.

Granato D A, Piguet P F. A mouse monoclonal IgE antibody anti bovine milk beta-lactoglobulin allows studies of allergy in the gastrointestinal tract. Clin Exp Immunol. 1986 March; 63(3):703-10.

Gopalakrishna K P, Macadangdang, B R, Rogers M B, Tometich J T, Firek B A, Baker R, Ji J, Burr AHP, Ma C, Good M, Morowitz M J, Hand T W. Maternal IgA protects against the development of necrotizing enterocolitis in preterm infants, Nat Med. 2019 July; 25(7):1110-1115.

Harrison M, Kilby A, Walker-Smith J A, France N E, Wood C B. Cows' milk protein intolerance: a possible association with gastroenteritis, lactose intolerance, and IgA deficiency. Br Med J. 1976 Jun. 19; 1(6024):1501-4.

Jones R M L, Schweikart F, Frutiger S, Jaton J-C, Hughes G J. Thiol-disulfide redox buffers maintain a structure of immunoglobulin A that is essential for optimal in vitro binding to secretory component. Biochimica et Biophysica Acta 1998; 1429:265-274.

Harumi J. Non-IgE Mediated Food Allergy. *Inflammation & Allergy—Drug Targets,* 2008, 7, 3, 173-180(8).

Kabir S. Jacalin: a jackfruit (*Artocarpus heterophyllus*) seed-derived lectin of versatile applications in immunobiological research. J Immunol Methods 1998, 212:193-211

Kelly C P, Chetham S, Keates S, Bostwick E F, Roush A M, Castagliuolo I, LaMont J T, Pothoulakis C. Survival of Anti-*Clostridium difficile* Bovine Immunoglobulin Concentrate in the Human Gastrointestinal Tract. Antimicrob Agents Chemother. 1997 February; 41(2):236-41.

Kohler G, Milstein C. Continuous Cultures of Fused Cells Secreting Antibody of Predetermined Specificity, Nature 1975; 256; 495-497.

Levy M, Kolodziejczyk A A, Thaiss C A, Elinav E. Dysbiosis and the immune system. Nat Rev Immunol. 2017 April; 17(4):219-232.

Lullau E., Heyse S., Vogel H., Marison I., von Stockar U., Kraehanbuhl J-P., Corthesy B., Antigen Binding Properties of Purified Immunoglulin A Antibodies, J. Biol. Chem. 1996; 271:16300-16309.

Nakajima Al, Vogelzang A, Maruya M, Miyajima M, Murata Ml, Son A, Kuwahara T, Tsuruyama T, Yamada S, Matsuura M5, Nakase H, Peterson D A, Fagarasan S, Suzuki K IgA regulates the composition and metabolic function of gut microbiota by promoting symbiosis between bacteria. J Exp Med. 2018 Aug. 6; 215(8):2019-2034.

Oncley J L, Melin M, Richert D A, Cameron J W, Gross P M, Jr., The Separation of the Antibodies, Isoagglutinins, Prothrombin, Plasminogen and (31-Lipoprotein into Subfractions of Human Plasma. J. Am. Chem. Soc. 1949; 71:541-550.

Possin M E, Morgan S, DaSilva D F, Tisler C, Pappas T E, Roberg K A, Anderson E, Evans M D, Gangnon R, Lemanske R F, Gern J E. The relationships among immunoglobulin levels, allergic sensitization, and viral respiratory illnesses in early childhood. Pediatr Allergy Immunol 2010: 21: 990-996.

Rogier, et al. Secretory antibodies in breast milk promote long-term intestinal homeostasis by regulating the gut microbiota and host gene expression (PNAS 2014 111 (8) 3074-3079.

Schwarze J, Cieslewicz G, Joetham A, L Sun L K, Sun W N, Chang T W, Hamelmann E, W. Gelfand E W. Antigen-specific Immunoglobulin-A Prevents Increased Airway Responsiveness and Lung Eosinophilia after Airway Challenge in Sensitized Mice. Am J Resp Crit Care Med 1998; 158:519-525.

Shimoda M, Inoue Y, Azuma N, Kanno C. Local antibody response in Peyer's patches to the orally administered dietary protein antigen. Biosci Biotechnol Biochem. 1999 December; 63(12):2123-9.

Simon M R, et al., Polyclonal antibody therapies for *Clostridium difficile* infection. Antibodies 2014; 3:272-288.

Strong L E, Blood Fractionation, pp. 576-602 in vol. 3, Kirk-Othmer Encyclopedia of Chemical Technology. Second Edition, H. F. Mark, J. J. McKetta, D. F. Othmer (eds), Interscience Publishers, NY 1963, pp. 576-602.

Symersky J, Novak J, McPherson D T, DeLucas L, Mestecky J. Expression of the recombinant human immunoglobulin J chain in *Escherichia coli*. Mol. Immunol. 2000; 37:133-140.

Trajkovski V, Ajdinski L, Spiroski M. Plasma concentration of immunoglobulin classes and subclasses in children with autism in the Republic of Macedonia: retrospective study. Croat Med J. 2004 December; 45(6):746-9.

Vighi G, Marcucci F, Sensi L, G. Di Cara G, Frati F. Allergy and the gastrointestinal system. *Clinical and Experimental Immunology,* 153 (Suppl. 1): 3-6, 2008.

Vojdani A. Detection of IgE, IgG, IgA and IgM antibodies against raw and processed food antigens. Nutr Metab (Lond). 2009 May 12; 6:22.

Walker A M, Kemp A S, Hill D J, Shelton M J. Features of transient hypogammaglobulinaemia in infants screened for immunological abnormalities. Arch Dis Child. 1994 March; 70(3): 183-186.

Wang M, Takeda K, Shiraishi Y, Okamoto M, Dakhama A, Joetham A, Gelfand E W. Peanut-induced intestinal allergy is mediated through a mast cell-IgE-FcepsilonRI-IL-13 pathway. J Allergy Clin Immunol. 2010 August; 126(2):306-16, 316.e1-12.

Yang P-C, Wang C-S, An Z-Y. A murine model of ulcerative colitis: induced with sinusitis-derived superantigen and food allergen. BMC Gastroenterology 2005, 5:6.

Yoon M Y, Yoon S S. Disruption of the Gut Ecosystem by Antibiotics. Yonsei Medical Journal. 2018, 59 (1):4.

Patent applications and publications mentioned in the specification are indicative of the levels of those skilled in the art to which the invention pertains. These applications and publications are incorporated herein by reference to the same extent as if each individual application or publication was specifically and individually incorporated herein by reference.

The foregoing description is illustrative of particular embodiments of the invention but is not meant to be a limitation upon the practice thereof. The following claims, including all equivalents thereof, are intended to define the scope of the invention.

The invention claimed is:

1. A process for treatment of necrotizing enterocolitis in a premature infant subject suffering therefrom, the process comprising:

purifying IgA from healthy human plasma;

modifying said IgA with recombinant human secretory component to form a purified mixture having only therapeutic effective components selected from the group consisting of dimeric secretory IgA, polymeric secretory IgA, and a combination thereof;

administering orally to the premature infant subject suffering from necrotizing enterocolitis said purified mixture; and allowing sufficient time for said purified mixture to treat the necrotizing enterocolitis in the premature infant subject.

2. The process of claim 1 wherein said purified mixture is manufactured by an industrial process comprising said recombinant human secretory component and natural human plasma-derived IgA dimers and higher polymers.

3. The process of claim 1 further comprising co-administration of isotonic agents.

4. The process of claim 1 wherein said IgA is a byproduct from pooled healthy human plasma following Cohn cold ethanol fractionation to produce a fraction III precipitate.

5. The process of claim 1 wherein said IgA is a byproduct of recovery of IgG from pooled healthy human plasma followed by ion exchange chromatography.

* * * * *